United States Patent
Fog et al.

(10) Patent No.: US 8,888,143 B2
(45) Date of Patent: Nov. 18, 2014

(54) TORQUE LIMITING FASTENING ASSEMBLIES AND FLUID COUPLING ASSEMBLIES INCLUDING THE SAME

(71) Applicant: Diba Industries, Inc., Danbury, CT (US)

(72) Inventors: Stephen C. Fog, New Canaan, CT (US); Gary C. Helstern, Newtown, CT (US)

(73) Assignee: Diba Industries, Inc., Danbury, CT (US)

( * ) Notice: Subject to any disclaimer, the term of this patent is extended or adjusted under 35 U.S.C. 154(b) by 44 days.

(21) Appl. No.: 13/625,336

(22) Filed: Sep. 24, 2012

(65) Prior Publication Data

US 2013/0076030 A1 Mar. 28, 2013

Related U.S. Application Data

(60) Provisional application No. 61/538,315, filed on Sep. 23, 2011.

(51) Int. Cl.
*F16L 37/18* (2006.01)
*F16L 19/07* (2006.01)
*F16L 19/025* (2006.01)

(52) U.S. Cl.
CPC .............. *F16L 19/07* (2013.01); *F16L 19/025* (2013.01)
USPC .......................................... 285/314; 285/309

(58) Field of Classification Search
USPC .......... 285/314, 304, 309, 384, 394, 395, 359
See application file for complete search history.

(56) References Cited

U.S. PATENT DOCUMENTS

| | | | |
|---|---|---|---|
| 4,738,401 A * | 4/1988 | Filicicchia | 239/600 |
| 5,020,949 A | 6/1991 | Davidson et al. | |
| 5,190,224 A * | 3/1993 | Hamilton | 239/600 |
| 6,398,128 B1 * | 6/2002 | Hamilton et al. | 239/71 |
| 7,299,725 B2 | 11/2007 | Helstern | |
| 7,954,857 B2 | 6/2011 | Helstern | |
| 7,984,933 B2 | 7/2011 | Helstern | |

* cited by examiner

*Primary Examiner* — Aaron Dunwoody
(74) *Attorney, Agent, or Firm* — Dinsmore & Shohl LLP

(57) ABSTRACT

Fluidic coupling assemblies include a fitting body having a single integral piece or separable pieces such as male and female fittings such as luer fittings. The assemblies further comprise a rotatable fastening assembly having a drive collar and a driven member, and at least one resilient member having a spring bias that defines a threshold torque of the rotatable fastening assembly. The spring bias may be directed axially or radially with respect to the longitudinal axis of the fluidic coupling assembly. The resilient member is configured to prevent overtightening of the fluidic coupling assembly by allowing the drive collar to rotate the driven member only when less than a threshold torque is applied. Rotation of the rotatable fastening assembly imparts a compressive force on the resilient member, and the resilient member yields when the compressive force exceeds the spring bias of the resilient member.

14 Claims, 13 Drawing Sheets

TORQUE LIMITING FASTENING ASSEMBLIES AND FLUID COUPLING ASSEMBLIES INCLUDING THE SAME

CROSS-REFERENCES TO RELATED APPLICATIONS

This application claims the benefit of priority under 35 U.S.C. §119(e) to U.S. Provisional Application Ser. No. 61/538,315, filed Sep. 23, 2011.

TECHNICAL FIELD

The present specification relates generally to fluid coupling devices and, more particularly, to torque limiting mechanisms and fluidic coupling assemblies including the torque limiting mechanisms.

BACKGROUND

Fluidic coupling devices are commonly used in many industries. In the healthcare industry, for example, it may be desirable to quickly establish a leak-free fluidic connection that can be connected and disconnected repeatedly. One type of fluidic coupling common in the healthcare industry is a locking luer connector. A locking luer connector generally includes a male portion that fits into a female portion and tightening means to properly seat the male portion in the female portion and secure the connection. If the tightening means include a threaded assembly that requires torque to operate, for example, excessive torque on the tightening means causes overtightening. The overtightening may result in a leaky connection, a failed connector, or a fluidic connection that is difficult to disconnect. The last of these problems may occur, for example, when a rather muscular technician connects the luer connector with a great amount of strength, and then a less physically gifted technician attempts to disconnect the luer connector. Similar problems exist with threaded stem-type fittings that may be used to connect tubing to a port, for example.

There remain ongoing needs for providing fluidic couplings having features that eliminate or avoid overtightening and the problems associated with overtightening.

SUMMARY

Against the above background, embodiments described herein are directed to fluidic coupling assemblies. The fluidic coupling assemblies may include a male fitting having an insert portion; a female fitting having a receiving portion adapted to accommodate the insert portion of the male fitting; a rotatable fastening assembly; and at least one resilient member having a spring bias that defines a threshold torque of the rotatable fastening assembly. The rotatable fastening assembly may include a drive collar having at least one driving surface and at least one collar abutment. The rotatable fastening assembly may also include a driven member at least partially accommodated within the drive collar. The driven member may have an internal threaded wall, at least one forcible surface, and at least one driven-member abutment. The female fitting may have a thread-engaging portion that engages the internal threaded wall of the driven member.

In such embodiments, rotation of the drive collar in a tightening direction with an applied torque imparts a compressive force on the at least one resilient member when the at least one forcible surface moves across the at least one driving surface. When the applied torque is less than the threshold torque, the compressive force is less than the spring bias, the at least one driving surface is forced against the at least one forcible surface, the driven member rotates with the drive collar, and the receiving portion of the female fitting is tightened into the insert portion of the male fitting. When the applied torque is greater than the threshold torque, the compressive force exceeds the spring bias, the at least one resilient member yields and allows the at least one driving surface to bypass the at least one forcible surface, the driven member does not rotate with the drive collar, and further tightening of the receiving portion of the female fitting into the insert portion of the male fitting is prevented. Rotation of the drive collar in a loosening direction forces the at least one driven-member abutment against the at least one collar abutment and forces the driven member to rotate with the drive collar.

Further embodiments described herein are directed to axially torque-limited fluidic coupling assemblies that may include a fitting body having a continuous channel defined therethrough. The fitting body may be a combination of a male fitting and a female fitting or may be a single integral piece. The continuous channel may define a longitudinal axis of the axially torque-limited fluidic coupling assembly. The axially torque-limited fluidic coupling assembly may further include an axial-compression fastening assembly. The axial-compression fastening assembly may include a drive collar and a toothed driven member. The drive collar is rotatable about the longitudinal axis and may include at least one collar tooth having a driving surface and a collar abutment. The toothed driven member may include at least one forcible tooth that has a forcible surface and a driven-member abutment. The axially torque-limited fluidic coupling assembly may further include mechanical threads that rotate when the toothed driven member rotates. The axially torque-limited fluidic coupling assembly may further include at least one resilient member having a spring bias that defines a threshold torque of the axial-compression fastening assembly.

In some embodiments of the axially torque-limited fluidic coupling assemblies, the axial-compression fastening assembly imparts an axially directed compressive force on the at least one resilient member when the forcible surface moves across the driving surface during rotation of the drive collar in a tightening direction with an applied torque. When the applied torque is less than the threshold torque, the compressive force is less than the spring bias, the driving surface is forced against the forcible surface, and the toothed driven member rotates with the drive collar. When the applied torque is greater than the threshold torque, the compressive force exceeds the spring bias, the at least one resilient member yields and allows the driving surface to bypass the forcible surface, and the toothed driven member does not rotate with the drive collar. Rotation of the drive collar in a loosening direction forces the driven-member abutment against the collar abutment and forces the toothed driven member to rotate with the drive collar.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
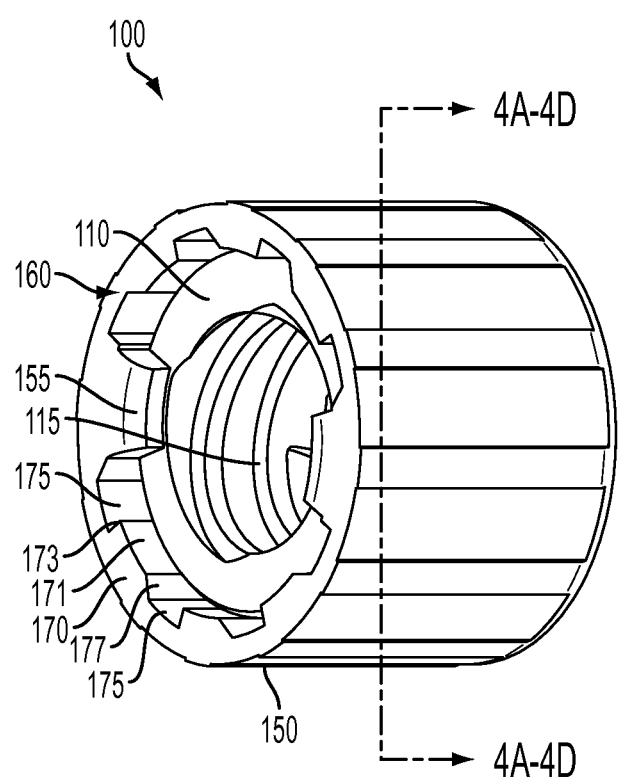
FIG. 1 is a perspective view of a radial-compression fastening assembly for fluidic couplings according to embodiments described herein.

The present specification describes torque limiting fastening assemblies for use with fluidic couplings such as, for example, locking luer assemblies. The torque limiting fastening assemblies each include at least one resilient member in cooperation with a drive collar and a driven member. The at least one resilient member ensures that the drive collar always rotates the driven member when a user rotates the drive collar in a loosening direction, but that the drive collar rotates the driven member only until a threshold torque is reached when a user rotates the drive collar with an applied torque in a tightening direction. Thereby, overtightening of the fluidic coupling may be prevented.

According to some embodiments, a fluidic coupling includes a male fitting, a female fitting, a fastening assembly, and at least one resilient member. The male fitting includes an insert portion, and the female fitting includes a receiving portion adapted to accommodate the insert portion of the male fitting. The fastening assembly includes a drive collar having at least one driving surface and at least one collar abutment. The fastening assembly also includes a driven member at least partially accommodated within the drive collar. The driven member has an internal threaded wall, at least one forcible surface, and at least one driven-member abutment. The at least one resilient member having a spring bias that defines a threshold torque of the fastening assembly. In some embodiments, each of the male fitting, the female fitting, the drive collar and the driven member of the fastening assembly are separate pieces. In other embodiments, certain components such as the male fitting and the driven member may be a single integral piece having the structural features of both the male fitting and the driven member combined. In some embodiments, the at least one resilient member may be a separate component, such as a coil spring or a compressible ring, for example, from each of the male fitting, the female fitting, the drive collar and the driven member of the fastening assembly. In other embodiments, the at least one resilient member may be a resilient portion of another component such as the drive collar or the driven member.

Illustrative embodiments of fluidic coupling assemblies now will be described with reference to the figures. It should be apparent that numerous modifications and variations to the illustrative embodiments are possible and, as such, that the descriptions herein and their depictions in one or more figures should not be regarded as limiting. First, illustrative embodiments of set-member fluidic coupling assemblies including radial-compression fastening assemblies will be described with reference to FIGS. 1-6B. Second, illustrative embodiments of sliding-member fluidic coupling assemblies including axial-compression fastening assemblies will be described with reference to FIGS. 7-13. Then, axially torque-limited fluidic coupling assemblies will be further described with reference to FIGS. 7-13, including embodiments of axially torque-limited port connection assemblies with reference to FIGS. 14-17. It should be apparent that the radial-compression fastening assemblies and the axial-compression fastening assemblies each include at least one resilient member having a spring bias that defines a threshold torque of the fastening assembly.

Figure 5:
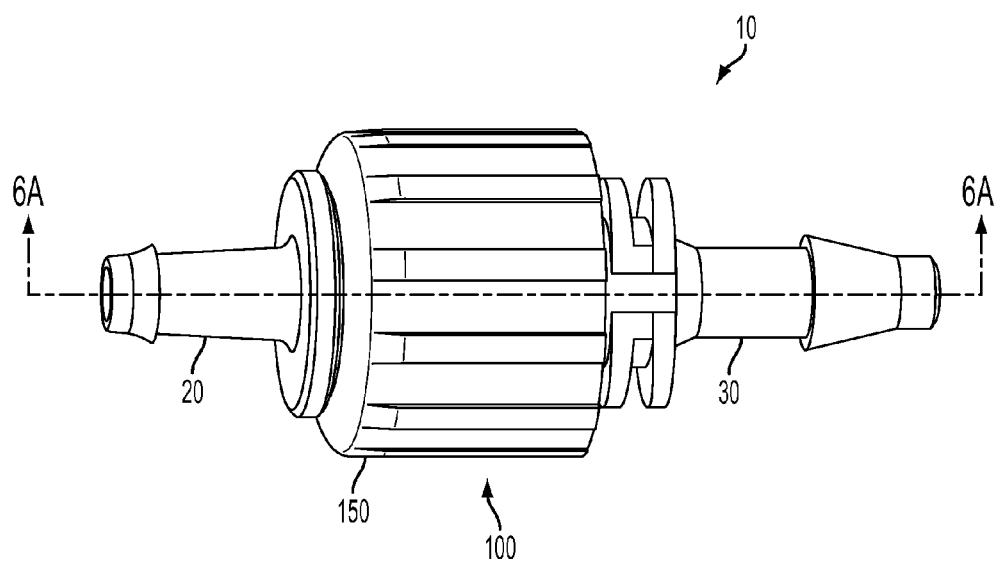
FIG. 5 is a perspective view of a fluidic coupling including a radial-compression fastening assembly according to one or more embodiments described herein.
Figure 6A:
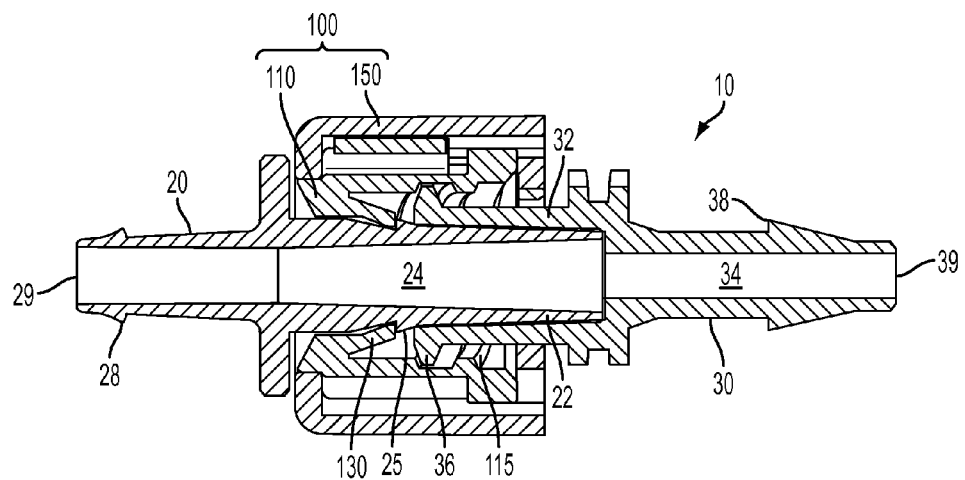
FIG. 6A is a cross-sectional plan view of the fluidic coupling of FIG. 5, according to an embodiment in which the male fitting and the driven member are separable pieces.

Referring to FIGS. 5 and 6A, according to some embodiments the fluidic coupling may be a set-member fluidic coupling 10. The set-member fluidic coupling 10 may include a male fitting 20 having an insert portion 22 and also may include a female fitting 30 having a receiving portion 32 adapted to accommodate the insert portion 22 of the male fitting 20. In preferred embodiments, the set-member fluidic coupling 10 may be a locking-luer coupling, the male fitting 20 may be a male luer, and the female fitting 30 may be a female luer.

The male fitting 20 has a male-fitting channel 24 defined through the male fitting 20, and the female fitting 30 has a female-fitting channel 34 defined through the female fitting 30. Thus, when the male fitting 20 and the female fitting 30 are connected, the male-fitting channel 24 and the female-fitting channel 34 form a continuous fluidic pathway defining a longitudinal axis of the set-member fluidic coupling 10. As used herein, unless otherwise indicated, the term "axial" refers to any direction parallel or substantially parallel to the longitudinal axis of the set-member fluidic coupling 10, whether toward the male fitting 20 or toward the female fitting 30. Likewise, unless otherwise indicated, the term "radial" refers to any direction perpendicular or substantially perpendicular to the longitudinal axis of the set-member fluidic coupling 10, whether toward the longitudinal axis or away from the longitudinal axis.

Figure 2:
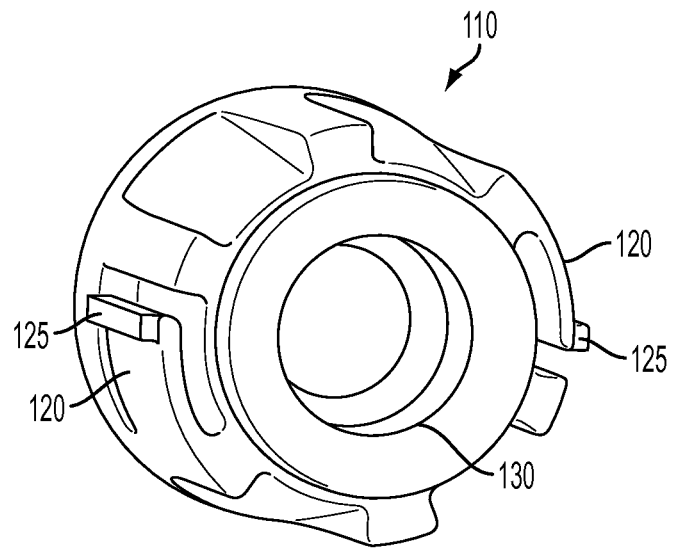
FIG. 2 is a perspective view of a driven member, a component of the radial-compression fastening assembly of FIG. 1.

The set-member fluidic coupling 10 may also include a rotatable fastening assembly such as a radial-compression fastening assembly 100. The radial-compression fastening assembly 100 may include a drive collar 150 and a driven member 110 at least partially accommodated within the drive collar 150. The driven member 110 may have an internal threaded wall 115. Additional structural components of the drive collar 150 and the driven member 110 will be described in greater detail below. The set-member fluidic coupling 10 also includes at least one resilient member having a spring bias that defines a threshold torque of the fastening assembly. In an illustrative embodiment described in detail below, the at least one resilient member may be a cantilever portion 120 of the driven member 110, as shown in FIG. 2. The female fitting 30 includes a thread-engaging portion 36 that engages the internal threaded wall 115 of the driven member 110.

With reference now to FIGS. 1-3 and 4A-4D, the radial-compression fastening assembly 100 now will be described in greater detail. Referring first to FIG. 1, the radial-compression fastening assembly 100 may include the driven member 110, which may be seated inside the drive collar 150, for example, by inserting the driven member 110 through collar end 160. The driven member 110 may be held inside the drive collar 150, for example, by a securing protrusion 155 of the drive collar 150. In some embodiments, the securing protrusion 155 prevents the driven member 110 from moving axially during tightening or loosening of the radial-compression fastening assembly 100. The driven member 110 comprises an internal threaded wall 115 that may be configured to engage a female fitting of a set-member fluidic coupling.

Referring to FIGS. 1 and 2, the driven member 110 further includes at least one resilient member. The resilient member of the driven member 110 of FIG. 2 is at least one cantilever portion 120 of the driven member 110. Though the driven member 110 of FIG. 2 includes two cantilever portions 120, in additional embodiments not should it should be understood that the driven member 110 may include only one cantilever portion 120 or may include more than two cantilever portions such as three, four, five, or more than five cantilever portions, for example. Each cantilever portion 120 may include a cantilever end 125. As a resilient member, each cantilever portion 120 is formed to have a spring bias, whereby the cantilever portion 120 may deflect inwardly (i.e., toward the center axis of the driven member 110) when an inwardly compressive force greater than the spring bias is applied to the cantilever end 125. When such a compressive force is relieved, the cantilever portion 120 may resiliently reacquire its original position before the inward deflection occurred. The driven member 110 also may have a coupling entrance 130 that accommodates a component of a fluidic coupling such as a female fitting, as will be described in greater detail below.

Figure 3:
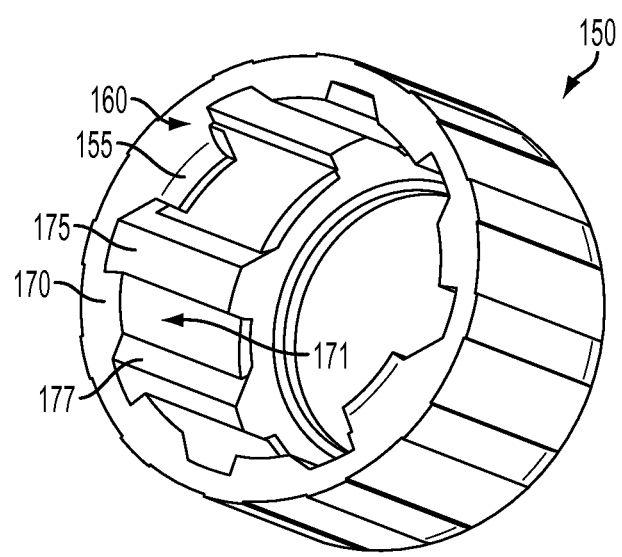
FIG. 3 is a perspective view of a driving collar, a component of the radial-compression fastening assembly of FIG. 1.

Referring to FIGS. 1 and 3, the drive collar 150 may include a plurality of collar protuberances 170 that define in the inner surfaces of the drive collar 150 a plurality of collar depressions 175 and collar slip walls 171 extending into the drive collar 150 from the collar end 160. The collar protuberances 170 each may include a driving surface 177 on one side of the collar protuberances 170 and a collar abutment 173 on the opposite side of the collar protuberances 170. Each of the collar depressions 175 may be interposed between a driving surface 177 and a collar abutment 173.

The operation of the radial-compression fastening assembly 100 is illustrated in FIGS. 4A-4D. The radial-compression fastening assembly 100 is in a neutral position in FIG. 4A, with the driven member 110 seated within the drive collar 150. The drive collar 150 may be rotated relative to the driven member 110 in either a counterclockwise tightening direction (+) or a clockwise loosening direction (−). It should be understood that the particular directions of tightening and loosening in FIGS. 4A-4D are illustrative only, not limiting, and that the drive collar 150 and the driven member 110 may be configured to be tightened clockwise and loosened counterclockwise, such as by reversing the thread slope of the internal threaded wall 115 (FIG. 6A) of the driven member 110.

Figure 4A:
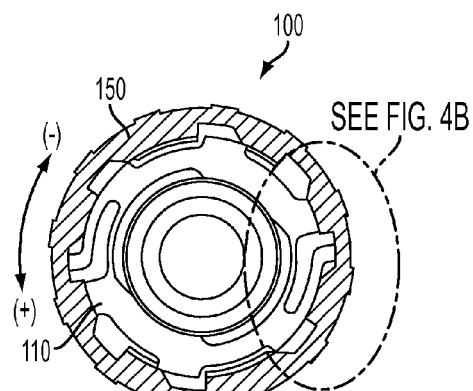
FIG. 4A is a cross-section of the radial-compression fastening assembly of FIG. 1.
Figure 4B:
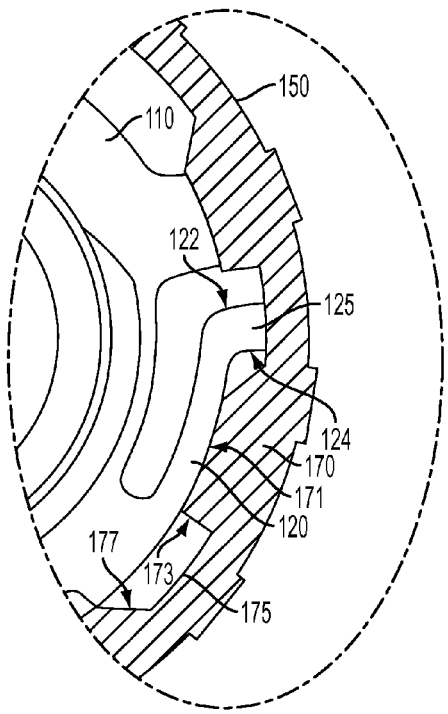
FIG. 4B is a detail view of the cross-section of FIG. 4A.

Components of the radial-compression fastening assembly 100 are shown in greater detail in FIG. 4B. The radial-compression fastening assembly 100 includes at least one resilient portion, cantilever portion 120, configured as a component of the driven member 110. In some embodiments, the cantilever portion 120 may include a cantilever end 125. In some embodiments, the cantilever end 125 may include a driven-member abutment 122 and a forcible surface 124. Though the cantilever end 125 in FIG. 4B has a curved shape, this should be regarded as illustrative only, and not limiting. In other embodiments not shown, for example, the cantilever portion may be substantially straight when not subjected to compressive forces. In such embodiments the cantilever end may have any angled or beveled profile defining a driven-member abutment configured to prevent rotation of the driven member 110 when the driven-member abutment contacts a collar abutment (described below) of the drive collar 150 and a forcible surface 124 that moves from friction against a driving surface (described below) of the drive collar 150.

The drive collar 150 may include a plurality of collar protuberances 170 (only one of which is labeled) that define a plurality of collar depressions 175 and collar slip walls 171. The collar protuberances 170 each may include a driving surface 177 on one side thereof and a collar abutment 173 on the opposite side thereof. Each of the collar depressions 175 may be interposed between a driving surface 177 and a collar abutment 173. The collar abutment 173 may be configured to arrest movement of the driven member 110 when the driven-member abutment 122 of the cantilever portion 120 contacts the collar abutment 173. The driving surface 177 may be configured to cause movement of the driven member 110 by friction against the forcible surface 124 of the cantilever portion 120.

Figure 4C:
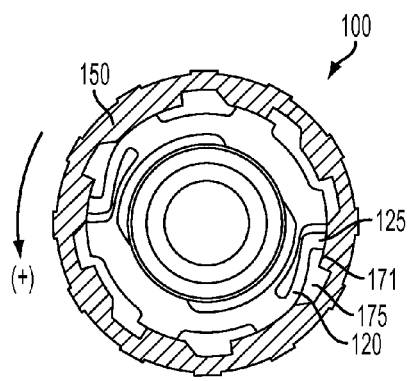
FIG. 4C illustrates movement of cantilever portions during tightening of the radial-compression fastening assembly of FIG. 1.

The at least one cantilever portion 120 of the driven member has resilience and a spring bias that defines a threshold torque of the radial-compression fastening assembly 100. Rotation of the drive collar 150 of the radial-compression fastening assembly 100 of FIG. 4A with an applied torque in the tightening direction (+) imparts a compressive force on the resilient member (i.e., the cantilever portion 120) when the at least one forcible surface moves across the at least one driving surface. The compressive force may be directed substantially or entirely in a radially inward direction. When the applied torque is less than the threshold torque, the compressive force is less than the spring bias of the cantilever portion 120, the at least one driving surface 177 is forced against the at least one forcible surface 124, and the driven member 110 rotates with the drive collar 150. Thereby, with reference to FIGS. 5 and 6A, in a set-member fluidic coupling 10 the receiving portion 32 of the female fitting 30 is tightened into the insert portion 22 of the male fitting 20. On the other hand, as illustrated in FIG. 4C, when the applied torque is greater than the threshold torque, the compressive force exceeds the spring bias of the cantilever portion 120, and the cantilever portion 120 yields (for example, by deflecting inwardly) to allow the driving surface 177 to bypass the at least one forcible surface 124, the driven member 110 does not rotate with the drive collar 150, and further tightening of the receiving portion 32 of the female fitting 30 into the insert portion 22 of the male fitting 20 is prevented. As shown in FIG. 4C, above the threshold torque the cantilever end 125 slides across collar slip walls 171 until the cantilever end 125 reaches the collar depressions 175. Owing to the resilience of the cantilever portion 120, when the cantilever end 125 does reach the collar depressions 175, the cantilever portion 120 may snap back from its deflected state. This snapping back may result in an audible click that informs the user that the threshold torque has been reached.

Figure 4D:
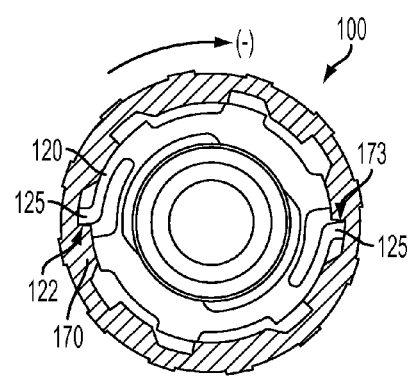
FIG. 4D illustrates positioning of cantilever portions during loosening of the radial-compression fastening assembly of FIG. 1.

Rotation of the drive collar 150 of the radial-compression fastening assembly 100 of FIG. 4A in the loosening direction (−) forces the at least one driven-member abutment 122 against the at least one collar abutment 173 and causes the driven member 110 to rotate with the drive collar 150. As illustrated in FIG. 4D, during rotation in the loosening direction (−), the driven-member abutment 122 of the cantilever end 125 of each cantilever portion 120 pushes against a collar abutment 173 of one of the collar protuberances 170. The cantilever portion 120 does not deflect under these circumstances, because the collar abutment 173 does not result in any inwardly directed compressive force on the cantilever end 125.

In embodiments not specifically depicted in FIGS. 1-3 and 4A-4D, it is contemplated that all structural components of the drive collar 150, particularly the at least one driving surface 177 and the at least one collar abutment 173, may instead be present as equivalent components of the driven member 110. In such embodiments, the drive collar 150 may include the resilient portion such as at least one cantilever portion 120 that includes a forcible surface 124 and a driven-member abutment 122. As such, it should be understood that when the at least one resilient member of a set-member fluidic coupling 10 is a portion of the radial-compression fastening assembly 100, the at least one resilient member may be a portion of the drive collar 150 or the driven member 110.

Referring again to FIGS. 5 and 6A, the radial-compression fastening assembly 100 may be a component of the set-member fluidic coupling 10. The set-member fluidic coupling 10 includes the radial-compression fastening assembly 100, the male fitting 20, and the female fitting 30. The male fitting 20 may include a male-fitting outside end 29, the insert portion 22, and, optionally, a male-fitting outer barb 28. A male-fitting channel 24 is defined through the male fitting 20. The female fitting 30 includes a female-fitting outside end 39, the receiving portion 32, and, optionally, a female-fitting outer barb 38. A female-fitting channel 34 is defined through the female fitting 30. The receiving portion 32 accommodates the insert portion 22, such that male-fitting channel 24 and female-fitting channel 34 form a continuous channel. The continuous channel establishes fluidic between communication between the male-fitting outside end 29 and the female-fitting outside end 39.

When the set-member fluidic coupling 10 is assembled, the coupling entrance 130 of the driven member 110 of the radial-compression fastening assembly 100 may engage a feature on the male fitting 20 such as a male-fitting inner barb 25, for example The receiving portion 32 may include a thread-engaging portion 36 that engages the internal threaded wall 115 of the driven member 110. Thus, when the radial-compression fastening assembly 100 is tightened by rotating the drive collar 150, the insert portion 22 is forced into the receiving portion 32. The resilient member comprising the cantilever portions 120 (see FIGS. 4A-4D), described above, prevents overtightening of the resulting fluidic coupling between the male fitting 20 and the female fitting 30.

Figure 6B:
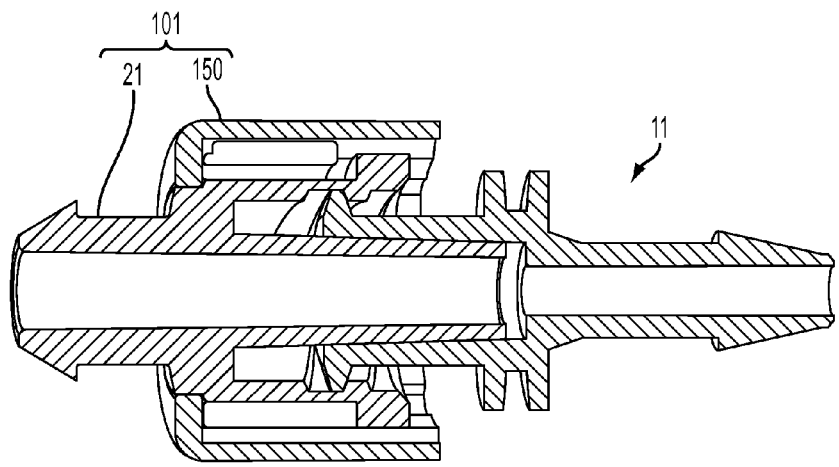
FIG. 6B is a cross-sectional plan view of an alternative embodiment of the fluidic coupling of FIG. 6A, in which the male fitting and the driven member are integral and molded as a single unitary piece.

An alternative embodiment of the set-member coupling 10 of FIG. 6A is provided in FIG. 6B as an integral set-member fluidic coupling 11. In the integral set-member fluidic coupling 11 the male fitting 20 and the driven member 110 that are two separable pieces in the set-member locking luer coupling 10 are formed as a single piece, namely, as an integral male-fitting driven member 21. Thus, in the integral set-member fluidic coupling 11 of FIG. 6B, an integral-fitting radial-compression fastening assembly 101 includes two pieces (i.e., the integral male-fitting driven member 21 and the drive collar 150) where three pieces (i.e., the male fitting 20, the driven member 110, and the drive collar 150) would be present using the radial-compression fastening assembly 100 of FIG. 6A. It should be understood that other components of the integral set-member fluidic coupling 11 not labeled in FIG. 6B may have the same structure and function as corresponding components of the lever-cap locking luer coupling 10 of FIG. 6A.

Having described above illustrative embodiments of set-member fluidic couplings including radial-compression fastening assemblies, illustrative embodiments of sliding-member fluidic couplings including axial-compression fastening assemblies now will be described with reference to FIGS. 7-13. Whereas in the set-member fluidic couplings described above, the driven member does not move substantially in the axial direction, in the sliding-member fluidic couplings the driven member does move in the axial direction to impart the compressive force against the at least one resilient member.

Referring to FIGS. 11A, 11B, 12, and 13, according to some embodiments the fluidic coupling may be a sliding-member fluidic coupling. Illustrative embodiments of sliding-member fluidic couplings may include a conical-collar fluidic coupling 12 of FIGS. 11A and 11B, a compressible-ring coupling 14 of FIG. 12, and a coil-spring coupling 15 of FIG. 13. Common to all of these embodiments, the sliding-member fluidic coupling may include a male fitting 20 having an insert portion 22 and also may include a female fitting 30 having a receiving portion 32 adapted to accommodate the insert portion 22 of the male fitting 20. In preferred embodiments, the sliding-member fluidic coupling may be a locking-luer coupling, the male fitting 20 may be a male luer, and the female fitting 30 may be a female luer.

The male fitting 20 has a male-fitting channel 24 defined through the male fitting 20, and the female fitting 30 has a female-fitting channel 34 defined through the female fitting 30. Thus, when the male fitting 20 and the female fitting 30 are connected, the male-fitting channel 24 and the female-fitting channel 34 form a continuous fluidic pathway defining a longitudinal axis of the set-member fluidic coupling 10. As described above, the term "axial" refers to any direction parallel or substantially parallel to the longitudinal axis of the set-member fluidic coupling 10, whether toward the male fitting 20 or toward the female fitting 30.

The sliding-member fluidic coupling may also include a rotatable fastening assembly such as an axial-compression fastening assembly 200. The axial-compression fastening assembly 200 may include an axially-forcing drive collar 250 and a toothed driven member 210 at least partially accommodated within the axially-forcing drive collar 250. The toothed driven member 210 may have an internal threaded wall 215. Additional structural components of the axially-forcing drive collar 250 and the toothed driven member 210 will be described in greater detail below. The set-member fluidic coupling also includes at least one resilient member having a spring bias that defines a threshold torque of the fastening assembly. In the illustrative embodiments described in detail below, the at least one resilient member may be, for example, a conical-spring portion 240 of the axially-forcing drive collar 250 (FIG. 11A), a compressible ring 260 (FIG. 12) or a coil spring 265 (FIG. 13). The female fitting 30 includes a thread-engaging portion 36 that engages the internal threaded wall 215 of the toothed driven member 210.

Figure 7:
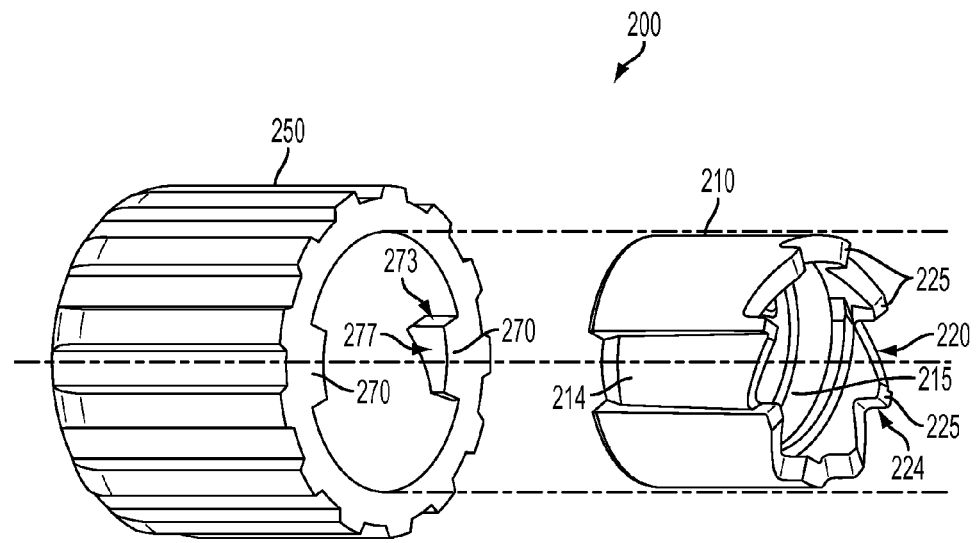
FIG. 7 is an exploded view of an axial-compression fastening assembly according to one or more embodiments described herein.
Figure 8:
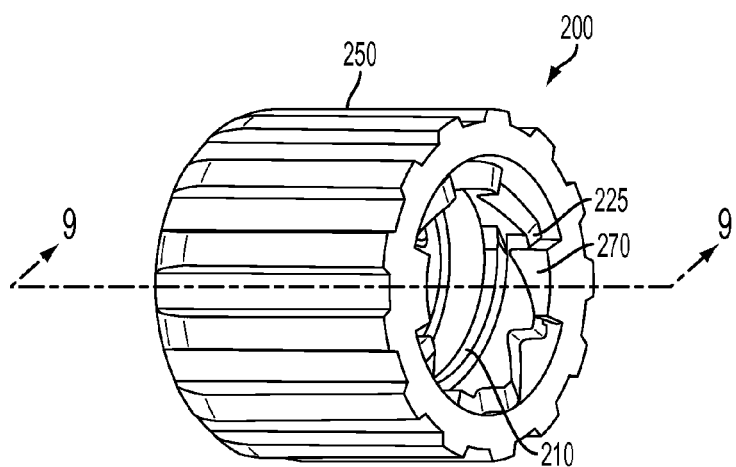
FIG. 8 is a perspective view of the axial-compression fastening assembly of FIG. 7 in its assembled state.

With reference now to FIGS. 7 and 8, the axial-compression fastening assembly 200 now will be described in greater detail. The axial-compression fastening assembly 200 includes a toothed driven member 210 that is insertable into an axially-forcing drive collar 250. The axially-forcing drive collar 250 includes collar teeth 270 that may be configured to slide over corresponding accommodating grooves 214 on the outer surfaces of the toothed driven member 210. The collar teeth 270 may include a collar abutment such as abutment face 273 and a driving surface such as driving face 277. The toothed driven member 210 may include a plurality of forcible teeth 225. Each of the forcible teeth 225 is defined by a driven-member abutment such as pushing wall 224 and a forcible surface such as tooth slope 220. The tooth slopes 220 are configured to mate with the driving face 277 of each of the collar teeth 270. The inner surfaces of the toothed driven member 210 may include an internal threaded wall 215 that may be configured to engage a thread-engaging portion of a female fitting of a sliding-member fluidic coupling, for example.

Figure 9:
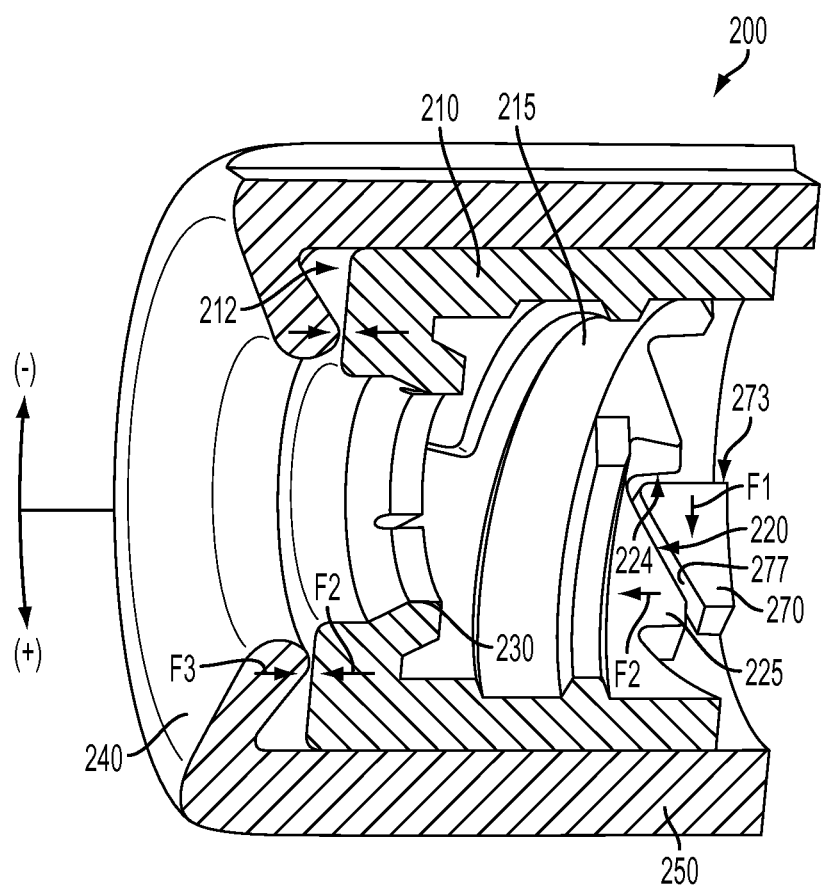
FIG. 9 is a cross-sectional perspective view of an embodiment of the axial-compression fastening assembly of FIG. 8, in which a drive collar includes a conical-spring portion as a resilient member.
Figure 10:
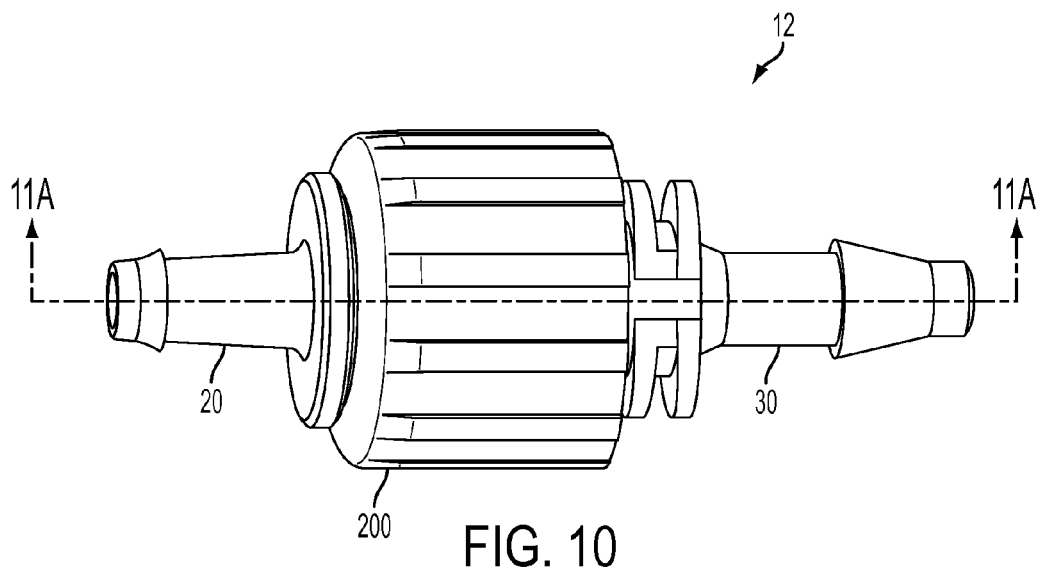
FIG. 10 is a perspective view of a fluidic coupling including an axial-compression fastening assembly according to one or more embodiments described herein.
Figure 11A:
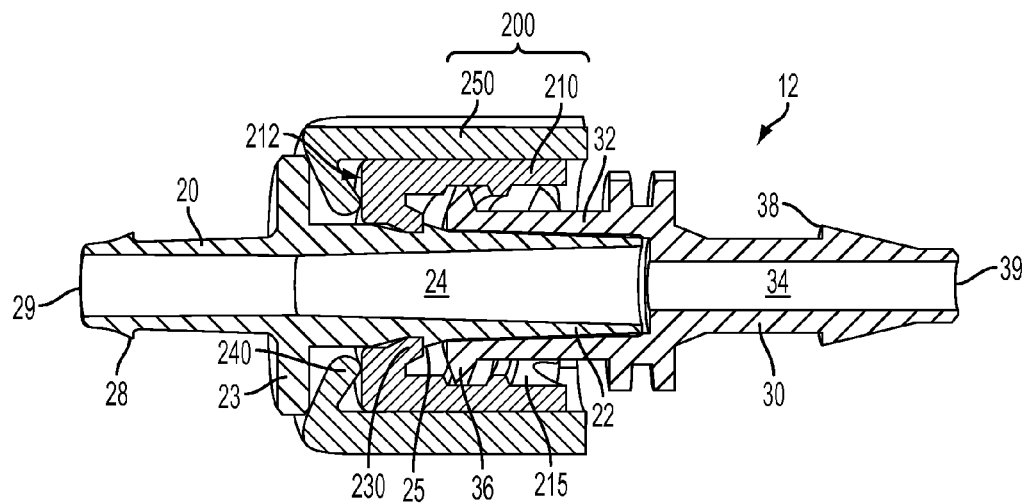
FIG. 11A is a cross-sectional plan view of the fluidic coupling of FIG. 10 according to one embodiment, in which the drive collar includes a conical-spring portion as a resilient member and the male fitting and the driven member are separable components.
Figure 11B:
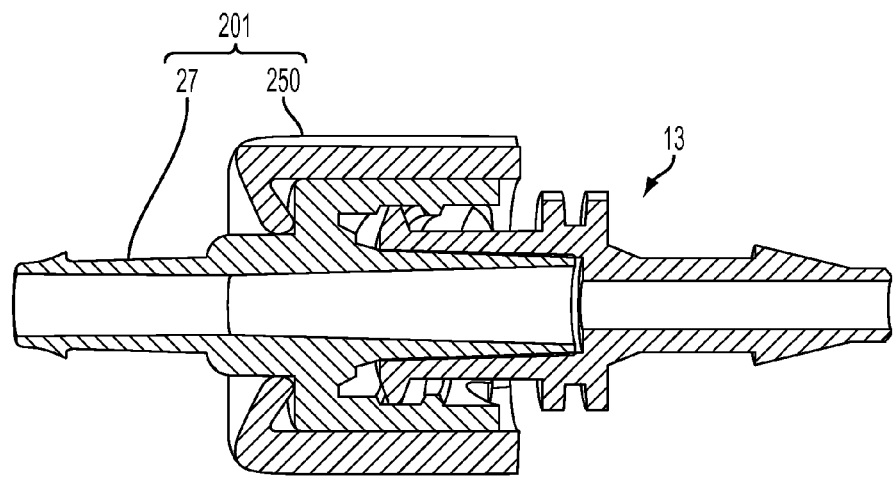
FIG. 11B is a cross-sectional plan view of a fluidic coupling according to an alternative embodiment to the embodiment of FIG. 11A, in which the drive collar includes a conical-spring portion as a resilient member and the male fitting and the driven member are a single integral component.

The views of the axial-compression fastening assembly 200 in FIGS. 7 and 8 are generally applicable to all of the illustrative embodiments herein of sliding-member fluidic couplings. In one particular embodiment, the side of the axial-compression fastening assembly 200 obscured in FIGS. 7 and 8 includes a conical-spring portion 240 as shown in FIG. 9. In other embodiments not shown, the side of the axial-compression fastening assembly 200 obscured in FIGS. 7 and 8 does not include the conical-spring portion.

Referring to FIG. 9, in some embodiments the axially-forcing drive collar 250 may include a resilient portion such as a conical-spring portion 240. The conical-spring portion 240 of the axially-forcing drive collar 250 has a spring bias F3 directed axially along the axial-compression fastening assembly 200 and can be compressed by the toothed driven member 210. The spring bias F3 defines a threshold torque of the axial-compression fastening assembly 200. Example rotational directions of the axially-forcing drive collar 250 relative to the toothed driven member 210 are illustrated in FIG. 9 with (+) representing a tightening direction and (−) representing a loosening direction. It should be understood that the particular directions of tightening and loosening in FIG. 9 are illustrative only, not limiting, and that the axially-forcing drive collar 250 and the toothed driven member 210 may be configured to be tightened and loosened in directions opposite those shown in FIG. 9, such as by reversing the thread slope of the internal threaded wall 215 of the toothed driven member 210.

Axial sliding of the toothed driven member 210 is illustrated in FIG. 9 in the context of the embodiment in which the axially-forcing drive collar 250 includes the conical-spring portion 240. In other embodiments described below, in which the axially-forcing drive collar 250 does not include a resilient member, the axial sliding motion of the toothed driven member 210 is identical.

As illustrated in FIG. 9, rotation of the axially-forcing drive collar 250 in the tightening direction (+) with an applied torque imparts a compressive force F2 on the conical-spring portion 240 when the at least one forcible surface (i.e., the tooth slope 220) moves across the at least one driving surface (i.e., the driving face 277). When the applied torque is less than the threshold torque, the compressive force F2 is less than the spring bias F3, the at least one driving surface (i.e., the driving face 277) is forced against the at least one forcible surface (i.e., the tooth slope 220), and the toothed driven member 210 rotates with the axially-forcing drive collar 250. Thereby, with reference to FIGS. 10 and 11A, in a conical-collar fluidic coupling 12 the receiving portion 32 of the female fitting 30 is tightened into the insert portion 22 of the male fitting 20. When the applied torque is greater than the threshold torque, the compressive force F2 exceeds the spring bias F3, the conical-spring portion 240 yields and allows the driving face 277 to bypass the tooth slope 220, and the toothed driven member 210 does not rotate with the axially-forcing drive collar 250. In the conical-collar fluidic coupling 12 of FIGS. 10 and 11A, for example, further tightening of the receiving portion 32 of the female fitting 30 into the insert portion 22 of the male fitting 20 is prevented once the applied torque exceeds the threshold torque.

In some embodiments, the conical-spring portion 240 may be configured to yield outwardly when an axially directed compressive force F2 exceeding the spring bias F3 of the conical-spring portion 240 is exerted on the conical-spring portion 240 by a distal compressing surface 212 of the toothed driven member 210. When the axially-forcing drive collar 250 is rotated in the tightening direction (+), the collar teeth 270 move downward (referring to the orientation of FIG. 9) and exert a downward force F1 (shown with a black arrow in FIG. 9). The downward force translates into the axially directed compressive force F2 by the pushing of the driving face 277 of the collar teeth 270 against the tooth slopes 220 (see FIG. 7) of the forcible teeth 225. When the axially directed compressive force F2 is less than the spring bias F3, the collar teeth 270 simply push on the forcible teeth 225 and cause the toothed driven member 210 to rotate along with the axially-forcing drive collar 250. However, once the axially directed compressive force F2 exceeds the threshold force F3, the toothed driven member 210 moves axially toward the conical-spring portion 240 and the conical-spring portion 240 yields in the direction of the axially directed compressive force F2, thereby allowing the collar teeth 270 to slip over the forcible teeth 225. When the collar teeth 270 slip over the forcible teeth 225, the toothed driven member 210 fails to continue rotating along with the axially-forcing drive collar 250. In some embodiments, a clicking sound will occur as an audible cue to the user that the threshold force has been reached.

Rotation of the axially-forcing drive collar 250 in a loosening direction forces the at least one driven-member abutment (i.e., pushing wall 224) against the at least one collar abutment (i.e., abutment face 273) and forces the toothed driven member 210 to rotate with the axially-forcing drive collar 250. In particular, the abutment face 273 of the axially-forcing drive collar 250 exerts a force against the pushing wall 224 of the toothed driven member 210 to cause the toothed driven member 210 to rotate.

Referring to FIGS. 10-13, the axial-compression fastening assembly 200 of FIGS. 7-9 may a component of a sliding-member fluidic coupling. In one embodiment, the sliding-member fluidic coupling may be a conical-collar fluidic coupling 12 (FIG. 11A). In another embodiment, the sliding-member fluidic coupling may be an integral conical-collar fluidic coupling 13 (FIG. 11B). In the integral conical-collar fluidic coupling 13 the male fitting 20 and the toothed driven member 210 are formed as a single piece, namely, as an integral male-fitting toothed driven member 27. Thus, in the integral conical-collar fluidic coupling 13 of FIG. 11B, an integral-fitting axial-compression fastening assembly 201 includes two pieces (i.e., the integral male-fitting toothed driven member 27 and the axially-forcing drive collar 250) where three pieces (i.e., the male fitting 20, the toothed driven member 210, and the axially-forcing drive collar 250) would be present using the axial-compression fastening assembly 200 of FIG. 11A.

Figure 12:
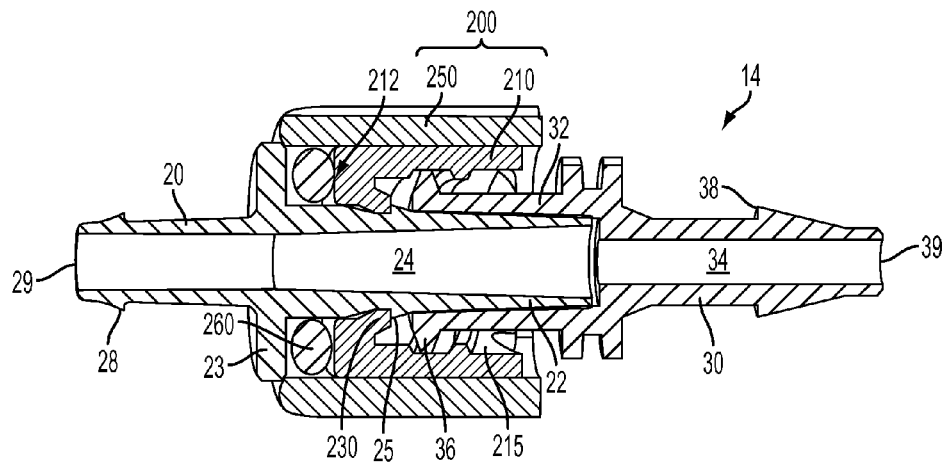
FIG. 12 is a cross-sectional plan view of the fluidic coupling of FIG. 10 according to one embodiment, in which the drive collar does not include a conical-spring portion and the fluidic coupling includes a compressible ring as a resilient member between the driven member and a transverse portion of the male fitting.
Figure 13:
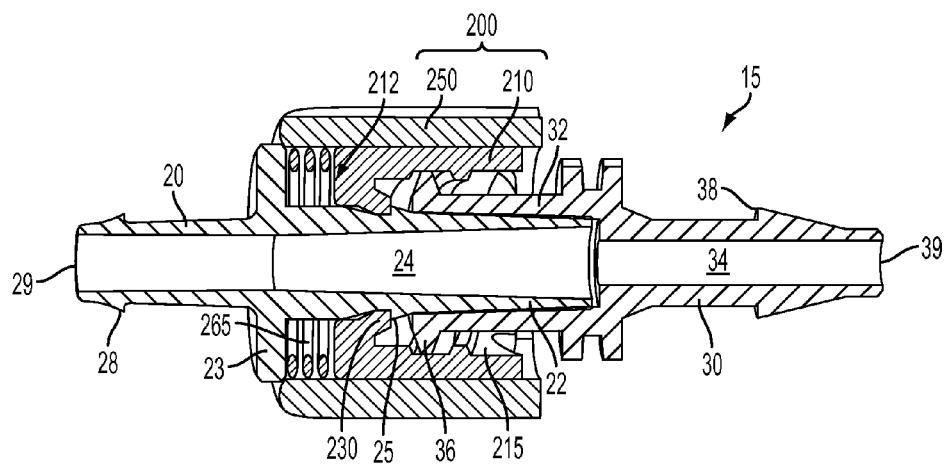
FIG. 13 is a cross-sectional plan view of the fluidic coupling of FIG. 10 according to one embodiment, in which the drive collar does not include a conical-spring portion and the fluidic coupling includes a coil spring as a resilient member between the driven member and a transverse portion of the male fitting.
Figure 14:
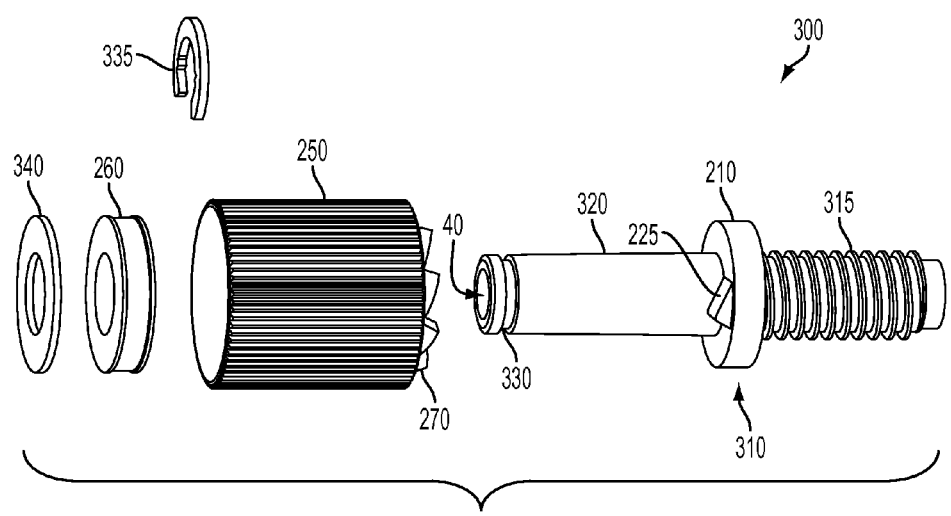
FIG. 14 is an exploded view of a fluidic coupling having an axial-compression fastening assembly according to one or more embodiments described herein.

In another embodiment, the sliding-member fluidic coupling may be a compressible-ring fluidic coupling 14 (FIG. 12). In the compressible-ring fluidic coupling 14, the at least one resilient member may be a compressible ring 260 such as an o-ring or other ring of suitable profile, not limited to the profile shown in FIG. 12. The compressible ring 260 may be made of any suitable material such as polymer, plastic, or metal. The toothed driven member 210 and the axially-forcing drive collar 250 may have the same structural features as shown in FIGS. 7 and 8, but the axially-forcing drive collar 250 preferably lacks the conical-spring portion 240 of FIG. 9. In some embodiments, the compressible ring 260 may be interposed between the distal compressing surface 212 of the toothed driven member 210 and a transverse portion 23 of the male fitting 20, such that compressive force during rotation of the axial-compression fastening assembly 200 compresses the compressible ring 260 between the distal compressing surface 212 and the transverse portion 23. In other embodiments, the compressible ring 260 may be interposed between the distal compressing surface 212 of the toothed driven member 210 and a flat roof portion (not shown) of the axially-forcing drive collar 250 that is not molded inwardly like the conical-spring portion 240 of FIG. 9. In other embodiments, the compressible spring may be held in place by a suitable clamp and/or washer (not shown) attached to the male fitting 20. The compressible ring 260 may have a spring bias that defines the threshold torque of the axial-compression fastening assembly 200, based on the compressive force above which the compressible ring 260 yields sufficiently to permit the driving face 277 of the axially-forcing drive collar 250 to bypass the tooth slope 220 of the toothed driven member 210.

In another embodiment, the sliding-member fluidic coupling may be a coil-spring coupling 15 (FIG. 13). In the coil-spring fluidic coupling 15, the at least one resilient member may be a coil spring 265 of with any suitable shape, size, or number of wrappings, not limited to the coil spring 265 as shown in FIG. 13. The coil spring 265 may be made of any suitable material such as polymer, plastic, or metal. The toothed driven member 210 and the axially-forcing drive collar 250 may have the same structural features as shown in FIGS. 7 and 8, but the axially-forcing drive collar 250 preferably lacks the conical-spring portion 240 of FIG. 9. In some embodiments, the coil spring 265 may be interposed between the distal compressing surface 212 of the toothed driven member 210 and a transverse portion 23 of the male fitting 20, such that compressive force during rotation of the axial-compression fastening assembly 200 compresses the coil spring 265 between the distal compressing surface 212 and the transverse portion 23. In other embodiments, the coil spring 265 may be interposed between the distal compressing surface 212 of the toothed driven member 210 and a flat roof portion (not shown) of the axially-forcing drive collar 250 that is not molded inwardly like the conical-spring portion 240 of FIG. 9. The coil spring 265 may have a spring bias that defines the threshold torque of the axial-compression fastening assembly 200, based on the compressive force above which the coil spring 265 yields sufficiently to permit the driving face 277 of the axially-forcing drive collar 250 to bypass the tooth slope 220 of the toothed driven member 210.

Each of the sliding-member fluidic couplings (i.e., the conical-collar fluidic coupling 12 of FIG. 11A, the integral conical-collar fluidic coupling 13 of FIG. 11B, the compressible-ring fluidic coupling 14 of FIG. 12, and the coil-spring coupling 15 of FIG. 13) includes an axial-compression fastening assembly 200 or a integral-fitting axial-compression fastening assembly 201, a male fitting 20, and a female fitting 30. The male fitting 20 includes a male-fitting outside end 29, a insert portion 22, and, optionally, a male-fitting outer barb 28. A male-fitting channel 24 is defined through the male fitting 20. The female fitting 30 includes a female-fitting outside end 39, a receiving portion 32, and, optionally, a female-fitting outer barb 38. A female-fitting channel 34 is defined through the female fitting 30. The receiving portion 32 accommodates the insert portion 22, such that male-fitting channel 24 and female-fitting channel 34 form a continuous channel. The continuous channel establishes fluidic between communication between the male-fitting outside end 29 and the female-fitting outside end 39.

When the sliding-member fluidic coupling according to any of the above embodiments is assembled, the coupling entrance 230 of the toothed driven member 210 of the axial-compression fastening assembly 200 may engage a feature on the male fitting 20 such as a male-fitting inner barb 25, for example. The receiving portion 32 comprises a thread-engaging portion 36 that engages the internal threaded wall 215 of the toothed driven member 210. Thus, when the axial-compression fastening assembly 200 is tightened by rotating the axially-forcing drive collar 250, the insert portion 22 is forced into the receiving portion 32. The resilient member comprising the conical-spring portion 240, described above, the compressible ring 260, or the coil spring 265, prevents overtightening of the resulting fluidic coupling between the male fitting 20 and the female fitting 30.

Referring to FIGS. 9-13 generally, in some embodiments, an axially torque-limited fluidic coupling assembly 12, 13, 14, 15 may include a fitting body having a continuous channel defined therethrough. The fitting body may be a combination of a male fitting 20 and a female fitting 30, and the continuous channel may be a combination of a male-fitting channel 24 and a female-fitting channel 34. The continuous channel may define a longitudinal axis of the axially torque-limited fluidic coupling assembly 12, 13, 14, 15. The axially torque-limited fluidic coupling assembly 12, 13, 14, 15 may further include an axial-compression fastening assembly 200. The axial-compression fastening assembly 200 may include a drive collar 250 and a toothed driven member 210. The drive collar 250 is rotatable about the longitudinal axis and may include at least one collar tooth 270 having a driving surface 277 and a collar abutment 273. The toothed driven member 210 may include at least one forcible tooth 225 that has a forcible surface 220 and a driven-member abutment 224. The axially torque-limited fluidic coupling assembly 12, 13, 14, 15 may further include mechanical threads such as an internal threaded wall 215, for example, that rotate when the toothed driven member 210 rotates. The axially torque-limited fluidic coupling assembly 12, 13, 14, 15 may further include at least one resilient member having a spring bias that defines a threshold torque of the axial-compression fastening assembly 200. The at least one resilient member may include, for example, a conical-spring portion 240 of the drive collar 250 (FIGS. 11A and 11B), a compressible ring 260 that is compressed by a distal compressing surface 212 of the toothed driven member 210 (FIG. 12), or a coil spring 265 that is compressed by a distal compressing surface 212 of the toothed driven member 210 (FIG. 13).

In the embodiments of the axially torque-limited fluidic coupling assembly 12, 13, 14, 15, the axial-compression fastening assembly 200 (a combination of the drive collar 250 and the toothed driven member 210) imparts an axially directed compressive force F2 (FIG. 9) on the at least one resilient member 240, 260, 265 when the forcible surface 220 moves across the driving surface 277 during rotation of the drive collar 250 in a tightening direction with an applied torque. In some embodiments, the at least one resilient member 240, 260, 265 may be interposed between a securing feature and a distal compressing surface 212 of the toothed driven member 210, such that and the compression force compresses the at least one resilient member 240, 260, 265 between the securing feature and the distal compressing surface. In illustrative embodiments, the securing feature may be the conical-spring portion 240 of the drive collar 250, a transverse portion 23 of the fitting body (such as on male fitting 20 in FIG. 11A), or a lip portion (not shown) of the drive collar 250 extending around a distal edge of the drive collar 250 in the same manner as a conical-spring portion but without resilient characteristics.

In some embodiments, the movement of the forcible surface 220 moves across the driving surface 277 during rotation of the drive collar 250 in a tightening direction causes the toothed driven member 210 to move toward the at least one resilient member 240, 260, 265. When the applied torque is less than the threshold torque, the compressive force is less than the spring bias, the driving surface 277 is forced against the forcible surface 220, the toothed driven member 210 rotates with the drive collar 250. Thereby, the axially torque-limited fluidic coupling assembly 12, 13, 14, 15 is tightened. When the applied torque is greater than the threshold torque, the compressive force exceeds the spring bias, the at least one resilient member 240, 260, 265 yields and allows the driving surface 277 to bypass the forcible surface 220, the toothed driven member 210 does not rotate with the drive collar 250. Thereby, further tightening of the axially torque-limited fluidic coupling assembly 12, 13, 14, 15 is prevented. Rotation of the drive collar 250 in a loosening direction forces the driven-member abutment 224 against the collar abutment 273 and forces the toothed driven member 210 to rotate with the drive collar 250. Thereby, the axially torque-limited fluidic coupling assembly 12, 13, 14, 15 is loosened.

Additional embodiments of axially torque-limited fluidic coupling assemblies will now be described with reference to FIGS. 14-17. Some embodiments of axially torque-limited fluidic coupling assemblies may include an axially torque-limited port connection assembly 300. As with the axially torque-limited fluidic coupling assemblies described above, the axially torque-limited port connection assembly 300 may include a fitting body 310 having a continuous channel 40 defined therethrough. In the axially torque-limited port connection assembly 300, however, the fitting body 310 may be constructed from a single unitary piece, rather than from a combination of a male fitting and a female fitting. The continuous channel 40 may define a longitudinal axis of the axially torque-limited port connection assembly 300.

The axially torque-limited port connection assembly 300 may further include an axial-compression fastening assembly 200. The axial-compression fastening assembly 200 may include a drive collar 250 and a toothed driven member 210. The toothed driven member 210 of the axially torque-limited port connection assembly 300 may be a portion of the fitting body 310, for example. The drive collar 250 is rotatable about the longitudinal axis and may include at least one collar tooth 270 having a driving surface 277 and a collar abutment 273. The toothed driven member 210 may include at least one forcible tooth 225 that has a forcible surface 220 and a driven-member abutment 224.

The axially torque-limited port connection assembly 300 may further include mechanical threads 315 that rotate when the toothed driven member 210 rotates. In some embodiments, the mechanical threads 315 of the axially torque-limited port connection assembly 300 may be disposed on the fitting body 310, for example. Though in FIGS. 14-17, the mechanical threads 315 are shown as male-type threads configured to be tightened into a female port, for example, the mechanical threads may also be provided on an internal portion of the fitting body 310, such as within the continuous channel 40, being configured to accept a male port. In either configuration, the mechanical threads 315 are configured to rotate when the toothed driven member 210 rotates. The fitting body 310 may include a proximal compressing surface 350, which will be described in greater detail below.

Figure 15:
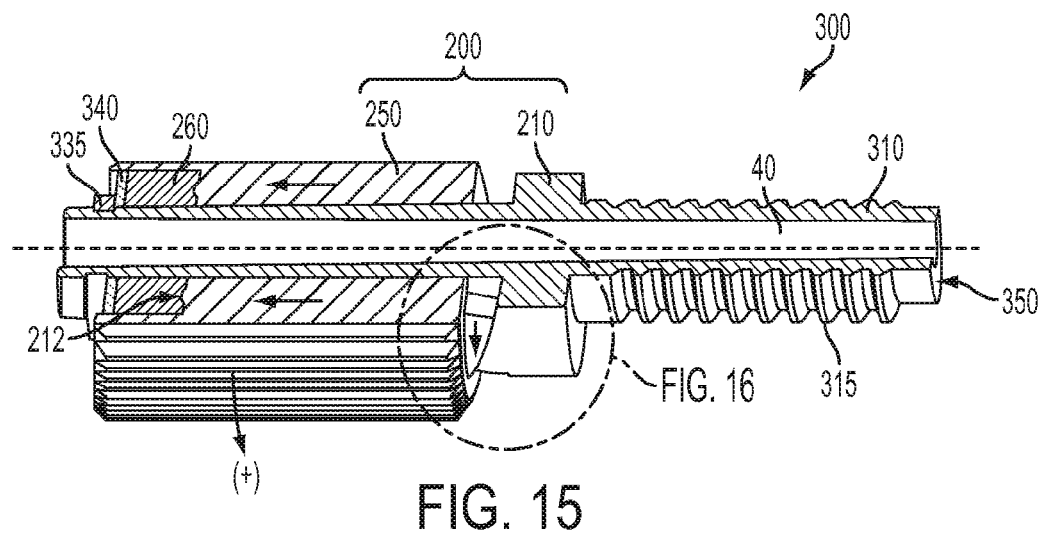
FIG. 15 is a cross-sectional view of the fluidic coupling of FIG. 14 in its assembled state.
Figure 16:
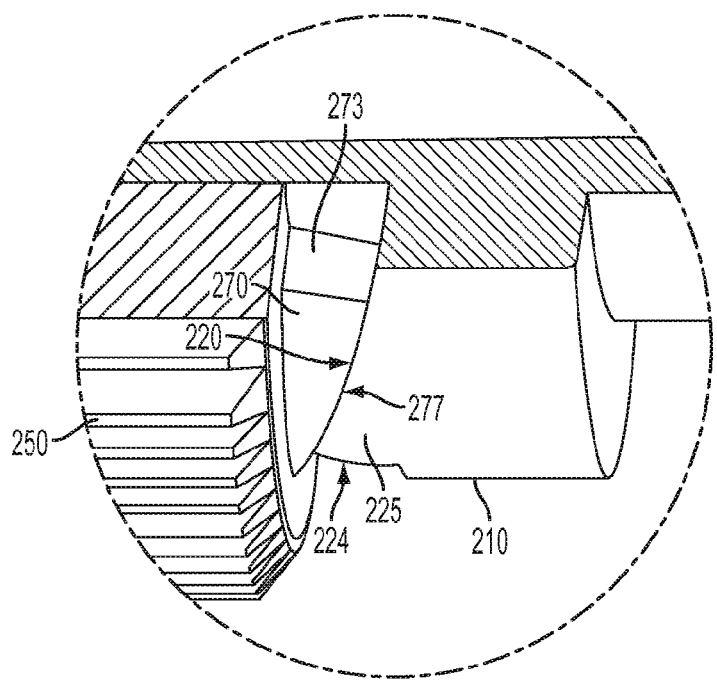
FIG. 16 is a detail view of teeth structures in the fluidic coupling of FIG. 14.

The axially torque-limited port connection assembly 300 may further include at least one resilient member having a spring bias that defines a threshold torque of the axial-compression fastening assembly 200. Though in FIGS. 14-17 illustrate one embodiment, in which the at least one resilient member is a compressible ring 260, in other embodiments the at least one resilient member may be a conical-spring portion 240 of the drive collar 250, as provided in FIG. 11A, or a coil spring 265, as provided in FIG. 13. The compressible ring 260 or the coil spring (FIG. 11A) may be compressed by a distal compressing surface 212 of the drive collar 250 when the drive collar 250 moves as shown in FIG. 15 turning tightening of the drive collar 250 in a tightening direction (+).

In some embodiments, the at least one resilient member may be secured inside the drive collar 250 using any suitable securing feature that holds the at least one resilient member inside the drive collar 250. For example, in one embodiment, the securing feature may be a securing washer 340 held in place around the fitting body 310 by a securing clamp 335. As in the illustrative embodiment of FIG. 14, the securing clamp 335 may be configured to latch onto a clamp groove 330 defined in a stem portion 320 of the fitting body, for example. In an embodiment not shown in FIG. 14, the securing feature may be, for example, a lip around the distal edge of the drive collar 250 that encloses at least a portion of the at least one resilient member inside the drive collar 250 while still allowing insertion of the at least one resilient member during assembly of the axially torque-limited port connection assembly 300. In another embodiment not shown in FIG. 14, the securing feature may include a barb or protrusion on the stem portion 320 of the fitting body 310, such that when the axially torque-limited port connection assembly 300 is assembled the barb or protrusion holds the at least one resilient member inside the drive collar 250.

As with the axially torque-limited fluidic coupling assemblies described above, in the axially torque-limited port connection assembly 300, the axial-compression fastening assembly 200 (a combination of the drive collar 250 and the toothed driven member 210) imparts an axially directed compressive force (illustrated in FIG. 15) on the at least one resilient member (such as the compressible ring 260) when the forcible surface 220 moves across the driving surface 277 during rotation of the drive collar 250 in a tightening direction with an applied torque. In some embodiments, the axially directed compressive force compresses the at least one resilient member (such as the compressible ring 260) between the securing feature (such as the securing washer 340 or other suitable feature described above) and the distal compressing surface 221. In some embodiments, when the applied torque is greater than the threshold torque, the drive collar 250 moves toward the at least one resilient member (such as the compressible ring 260) and the toothed driven member 210 is stationary. When the applied torque is less than the threshold torque, the compressive force is less than the spring bias, the driving surface 277 is forced against the forcible surface 220, and the toothed driven member 210 rotates with the drive collar 250. Thereby, the axially torque-limited port connection assembly 300 is tightened. When the applied torque is greater than the threshold torque, the compressive force exceeds the spring bias, the at least one resilient member (such as the compressible ring 260) yields and allows the driving surface 277 to bypass the forcible surface 220, the toothed driven member 210 does not rotate with the drive collar 250. Thereby, further tightening of the axially torque-limited port connection assembly 300 is prevented. Rotation of the drive collar 250 in a loosening direction forces the driven-member abutment 224 against the collar abutment 273 and forces the toothed driven member 210 to rotate with the drive collar 250. Thereby, the axially torque-limited port connection assembly 300 is loosened.

Figure 17:
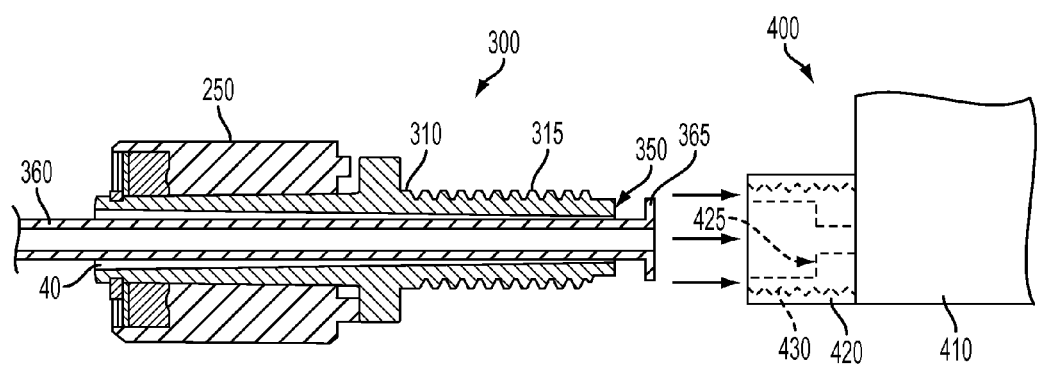
FIG. 17 is a cross-sectional plan view of the fluidic coupling of FIG. 14, illustrating connection of the fluidic coupling to a port using a tubing insert.

Referring with particularity to FIG. 17, in some embodiments the axially torque-limited port connection assembly 300 may further include a tubing insert 360. The tubing insert 360 may be a rigid or semi-rigid piece of tubing of any desired length and may have an outside diameter chosen such that the tubing insert 360 fits within the continuous channel 40 of the fitting body 310. The tubing insert 360 may include a compression portion 365. In some embodiments, the compression portion 365 may be configured as a flanged or flared end of the tubing insert, as shown in FIG. 17. In other embodiments not shown, the compression portion may include any of the compressible ferrule configurations described in commonly-owned U.S. Pat. No. 7,954,857, which document is incorporated herein by reference in its entirety. Thus, in some embodiments the axially torque-limited port connection assembly 300 having the tubing insert 360 may be connectable to a fluidic device 400 having a main body 410 that includes a connection port 420. The connection port 420 may include port threads 430 that mate with the mechanical threads 315 of the fitting body 310. The connection port 420 also may include a port compression wall 425 configured such that, when the axially torque-limited port connection assembly 300 is tightened into the connection port 420, the compression portion 365 of the tubing insert 360 is compressed against the port compression wall 425 of the connection port 420 by the proximal compressing surface 350 of the fitting body 310 to establish a leak-proof fluidic connection.

Thus, various embodiments of fluidic coupling assemblies have been described in detail. Illustrative embodiments of the fluidic coupling assemblies include set-member fluidic coupling assemblies, sliding-member fluidic coupling assemblies, and axially torque-limited fluidic coupling assemblies. Each fluidic coupling includes a resilient member that functions as torque-limiting mechanism to a fastening assembly of the fluidic coupling, thereby avoiding overtightening of the fluidic coupling and the problems inherent with overtightening of the fluidic coupling. In some embodiments, the fastening assembly is a radial-compression fastening assembly with one or more cantilever-type resilient member. In other embodiments, the fastening assembly is an axial-compression fastening assemblies having a resilient member such as a conical-spring portion, a compressible ring, or a coil spring, for example. The embodiments of fluidic coupling assemblies described herein are believed to eliminate or avoid overtightening and the problems associated with overtightening, as described through non-limiting illustrative embodiments of locking luer connectors and various port-type connectors.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment.

For the purposes of describing and defining the present invention it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

What is claimed is:

1. An axially torque-limited fluidic coupling assembly comprising:
   a fitting body having a stem portion and a continuous channel defined through the fitting body and the stem portion thereof, the continuous channel defining a longitudinal axis of the fluidic coupling assembly;
   an axial-compression fastening assembly comprising:
      a drive collar that is rotatable about the longitudinal axis around the stem portion of the fitting body and that comprises at least one collar tooth, the at least one collar tooth having a sloped driving surface and a collar abutment; and a toothed driven member portion of the fitting body comprising at least one forcible tooth, the at least one forcible tooth having a sloped forcible surface and a driven-member abutment;

mechanical threads on the fitting body that rotate when the toothed driven member portion of the fitting body rotates; and at least one resilient member having a spring bias that defines a threshold torque of the axial-compression fastening assembly, wherein:

rotation of the drive collar in a tightening direction with an applied torque imparts an axially directed compressive force from the drive collar on the at least one resilient member when the sloped forcible surface of the forcible tooth is forced against the sloped driving surface of the collar tooth;

when the applied torque is less than the threshold torque, the compressive force is less than the spring bias, the sloped driving surface is forced against and moves the sloped forcible surface, and the toothed driven member rotates with the drive collar in the tightening direction;

when the applied torque is greater than the threshold torque, the compressive force exceeds the spring bias, the at least one resilient member yields and allows the sloped driving surface to bypass the sloped forcible surface, and the toothed driven member does not rotate with the drive collar;

rotation of the drive collar in a loosening direction forces the driven-member abutment against the collar abutment and forces the toothed driven member to rotate with the drive collar in the loosening direction.

2. The axially torque-limited fluidic coupling assembly of claim 1, wherein:

the at least one resilient member is interposed between a securing feature around the stem portion of the fitting body and a distal compressing surface of the drive collar; and the axially directed compressive force compresses the at least one resilient member between the securing feature and the distal compressing surface.

3. The axially torque-limited fluidic coupling assembly of claim 2, wherein the compressive force is imparted by axial movement of the drive collar toward the at least one resilient member and away from the toothed driven member.

4. The axially torque-limited fluidic coupling assembly of claim 2, wherein the at least one resilient member is a compressible ring.

5. The axially torque-limited fluidic coupling assembly of claim 2, wherein the at least one resilient member is a coil spring.

6. The axially torque-limited fluidic coupling assembly of claim 2, wherein the securing feature comprises a securing washer held in place around the fitting body by a securing clamp latched into a clamp groove defined in the stem portion of the fitting body.

7. The axially torque-limited fluidic coupling assembly of claim 1, further comprising a tubing insert inserted through the continuous channel.

8. The axially torque-limited fluidic coupling assembly of claim 7, wherein the tubing insert comprises a compression portion configured to be compressed against a port compression wall of a connection port of a fluidic device by a proximal compressing surface of the fitting body.

9. The axially torque-limited fluidic coupling assembly of claim 1, wherein the mechanical threads are disposed on the fitting body and are configured to mate with port threads of a connection port of a fluidic device.

10. An axially torque-limited port connection assembly comprising:

a fitting body comprising:

a toothed driven member portion between a stem portion of the fitting body and a threaded portion of the fitting body;

at least one forcible tooth on the toothed driven member portion, the at least one forcible tooth having a sloped forcible surface and a driven-member abutment;

mechanical threads of the threaded portion that rotate when the toothed driven member portion rotates, the mechanical threads being configured to mate with port threads of a connection port;

a continuous channel defined through stem portion, the toothed driven member portion, and the threaded portion, the continuous channel defining a longitudinal axis of the fluidic coupling assembly;

a drive collar provided around the stem portion of the fitting body, the drive collar being rotatable about the longitudinal axis and comprising:

at least one collar tooth having a sloped driving surface and a collar abutment; and a distal compressing surface; and at least one resilient member compressible between the distal compressing surface of the drive collar and a securing feature that secures the at least one resilient member in the drive collar, the at least one resilient member having a spring bias that defines a threshold torque of the axial-compression fastening assembly, wherein:

rotation of the drive collar in a tightening direction with an applied torque compresses the at least one resilient member between the securing feature and the distal compressing surface of the drive collar when the sloped forcible surface of the forcible tooth is forced against the sloped driving surface of the collar tooth;

when the applied torque is less than the threshold torque, the compressive force is less than the spring bias, the sloped driving surface is forced against and moves the sloped forcible surface, and the toothed driven member rotates with the drive collar in the tightening direction;

when the applied torque is greater than the threshold torque, the compressive force exceeds the spring bias, the at least one resilient member yields, the sloped driving surface bypasses the sloped forcible surface, and the toothed driven member does not rotate with the drive collar; and rotation of the drive collar in a loosening direction forces the driven-member abutment against the collar abutment and forces the toothed driven member to rotate with the drive collar in the loosening direction.

11. The axially torque-limited port connection assembly of claim 10, wherein the at least one resilient member is a compressible ring or a coil spring.

12. The axially torque-limited port connection assembly of claim 10, wherein the securing feature comprises a securing washer held in place around the fitting body by a securing clamp latched into a clamp groove defined in the stem portion of the fitting body.

13. The axially torque-limited port connection assembly of claim 10, further comprising a tubing insert inserted through the continuous channel.

14. The axially torque-limited port connection assembly of claim 13, wherein the tubing insert comprises a compression portion configured to be compressed against a port compression wall of a connection port of a fluidic device by a proximal compressing surface of the fitting body.

* * * * *